(12) United States Patent
Dooley et al.

(10) Patent No.: US 10,048,754 B2
(45) Date of Patent: Aug. 14, 2018

(54) LOCALIZED HAPTIC RESPONSE

(71) Applicant: Grayhill, Inc., La Grange, IL (US)

(72) Inventors: Kevin M Dooley, Chicago, IL (US); Robert F Kerner, Chicago, IL (US)

(73) Assignee: GRAYHILL, INC., Lagrange, IL (US)

( * ) Notice: Subject to any disclaimer, the term of this patent is extended or adjusted under 35 U.S.C. 154(b) by 100 days.

(21) Appl. No.: 14/470,284

(22) Filed: Aug. 27, 2014

(65) Prior Publication Data
US 2016/0062461 A1 Mar. 3, 2016

(51) Int. Cl.
*G06F 3/041* (2006.01)
*G06F 3/01* (2006.01)
*G06F 1/16* (2006.01)
*A61B 8/00* (2006.01)

(52) U.S. Cl.
CPC .......... *G06F 3/016* (2013.01); *G06F 1/1684* (2013.01); *A61B 8/467* (2013.01)

(58) Field of Classification Search
None
See application file for complete search history.

(56) References Cited

U.S. PATENT DOCUMENTS

| | | | | |
|---|---|---|---|---|
| 6,388,655 | B1* | 5/2002 | Leung | G01L 1/20 341/34 |
| 2005/0052425 | A1* | 3/2005 | Zadesky | G06F 3/0338 345/173 |
| 2008/0012837 | A1* | 1/2008 | Marriott | G06F 3/03547 345/173 |
| 2008/0100568 | A1* | 5/2008 | Koch | G06F 3/016 345/156 |
| 2009/0072662 | A1* | 3/2009 | Sadler | G06F 1/3203 310/319 |
| 2010/0090813 | A1* | 4/2010 | Je | G06F 3/016 340/407.2 |
| 2011/0095877 | A1* | 4/2011 | Casparian | G06F 3/016 340/407.2 |
| 2012/0038471 | A1* | 2/2012 | Kim | H04N 1/00411 340/407.2 |
| 2014/0071079 | A1* | 3/2014 | Heubel | G06F 3/041 345/173 |

\* cited by examiner

*Primary Examiner* — William Boddie
*Assistant Examiner* — Bipin Gyawali
(74) *Attorney, Agent, or Firm* — K&L Gates LLP

(57) ABSTRACT

Touch interfaces for electronic devices including one or more tactile response mechanisms. The tactile response mechanisms receive user input and provide a tactile response to the user to indicate that the user has selected a particular location or selectable area on the interface. The underside of the interface includes recesses and/or channels corresponding to on each specific touch or selectable area that localize the tactile response to the individual selectable areas.

12 Claims, 10 Drawing Sheets

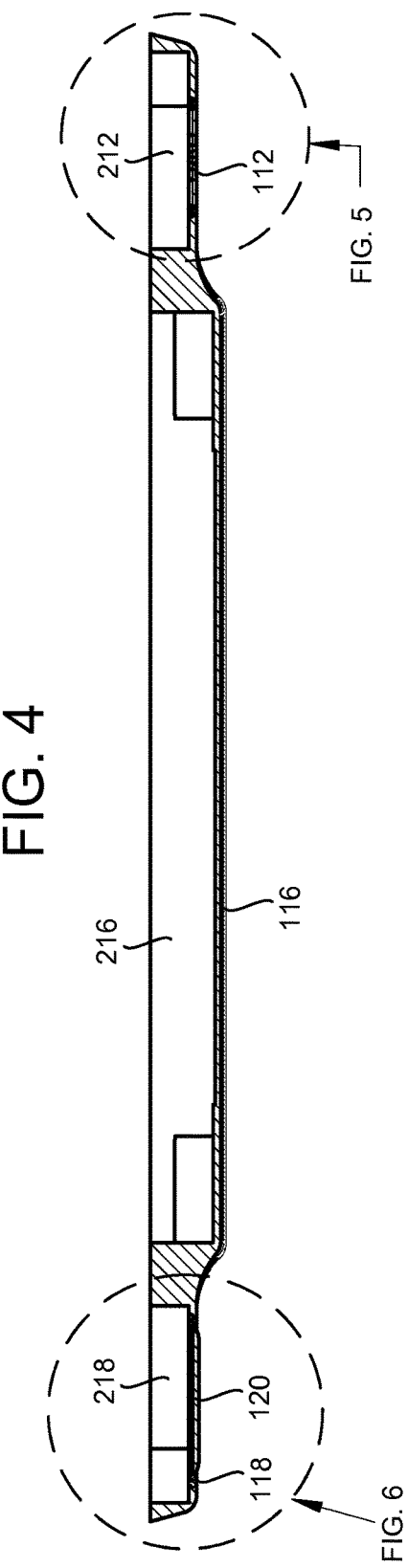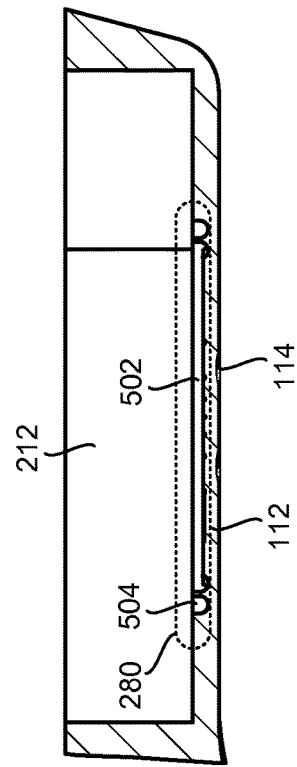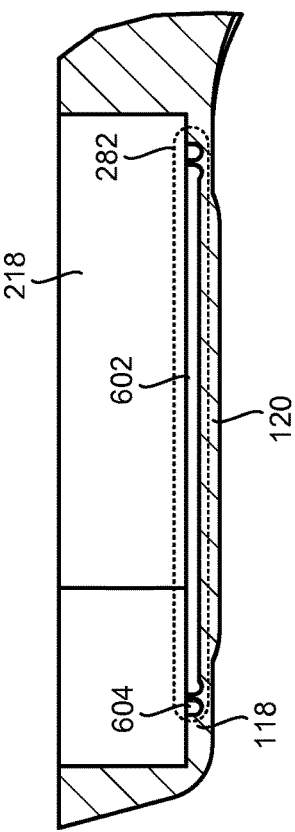

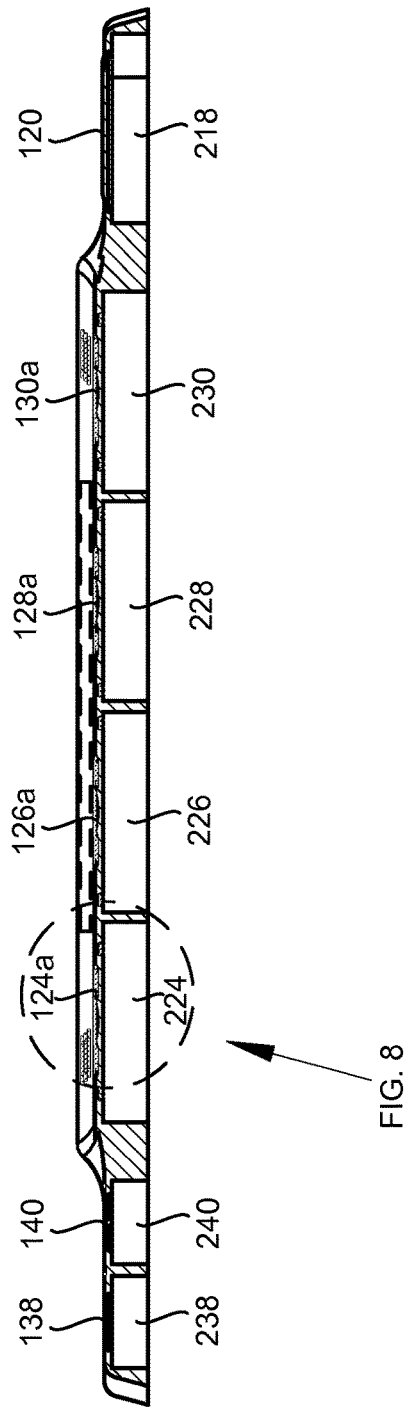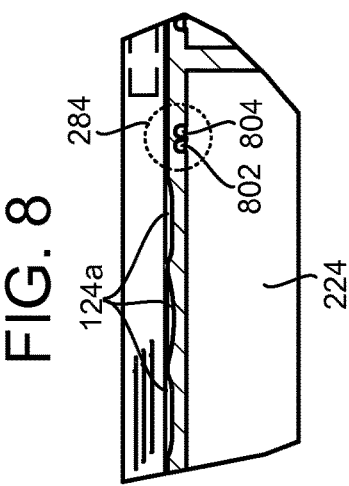

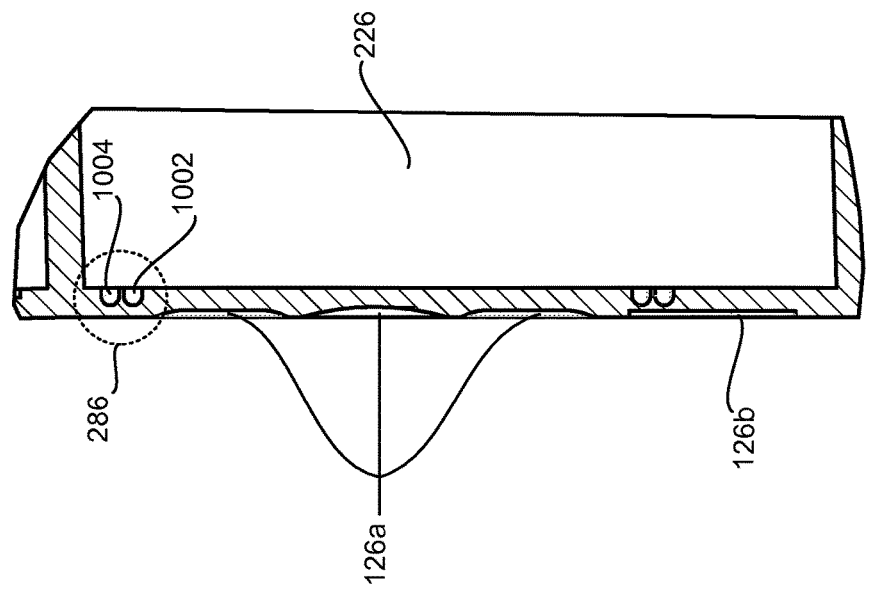
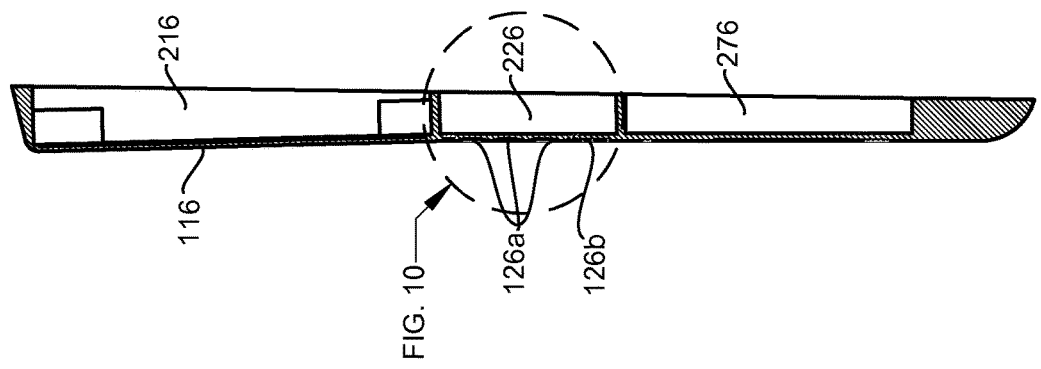

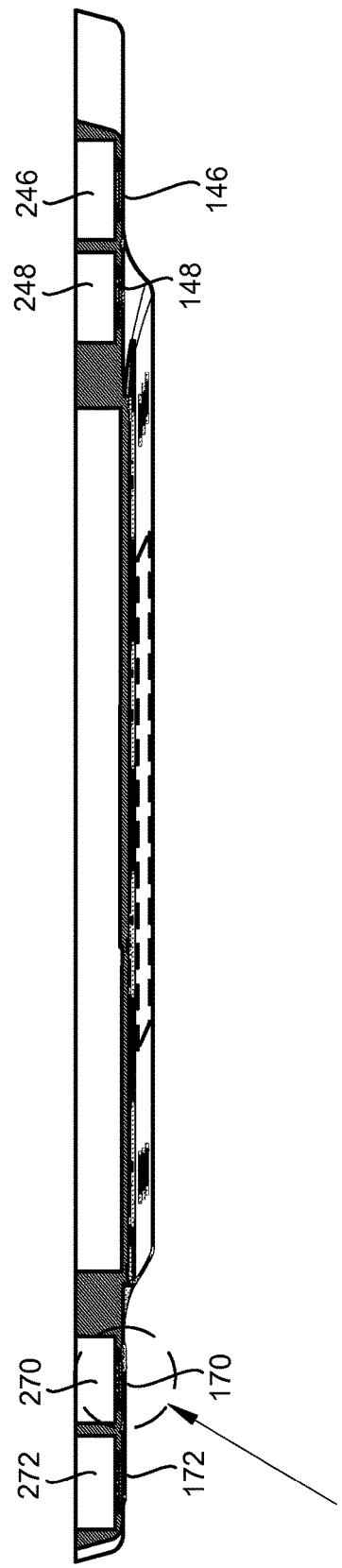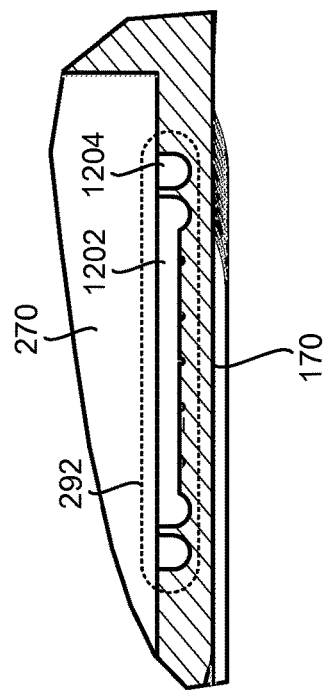

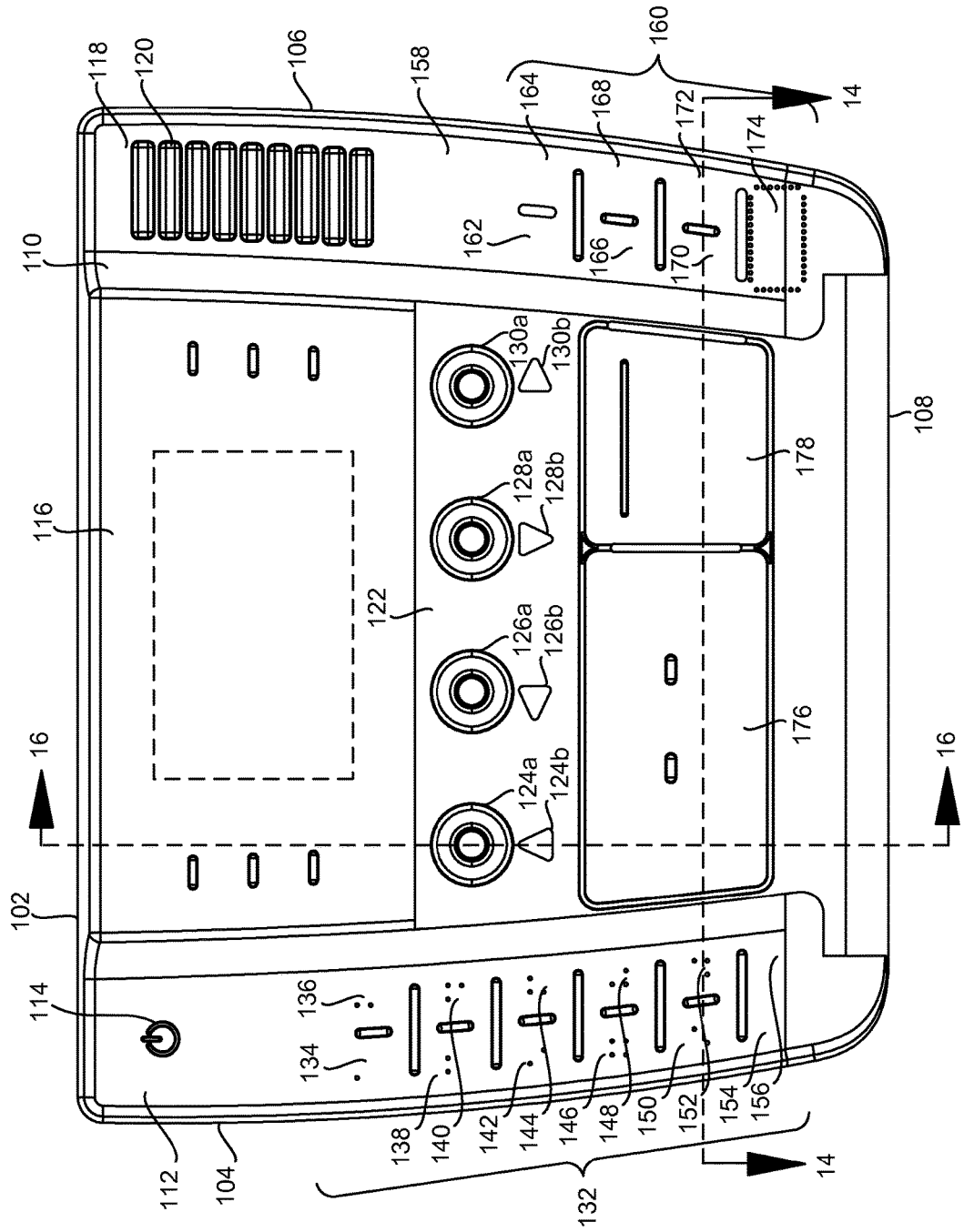

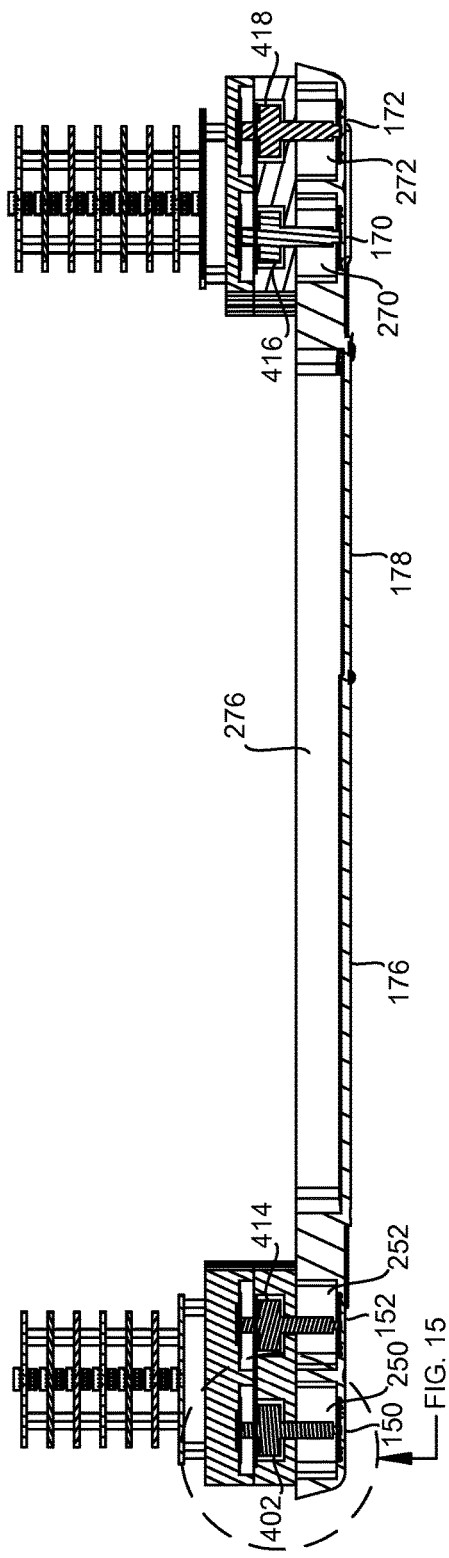
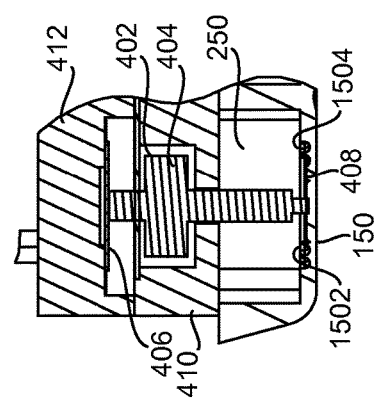

LOCALIZED HAPTIC RESPONSE

TECHNICAL FIELD

The present application relates generally to touch interfaces for electronic devices, and more particularly to touch interfaces adapted to provide a localized tactile feedback response.

BACKGROUND

Conventional electronic devices, such as, mobile phones and tablet computers, have touch-screens. Theses touch-screens may in some instances provide a tactile response to a user when the user touches a button or other icon of the touch-screen. This provides the user with confirmation that the button/icon has been selected. However, this tactile response typically vibrates the whole device or areas adjacent to the area selected.

Additionally, cleanliness and ease of cleaning electronic devices used in the medical field is important. Traditional electronic devices used in the medical field may include keyboards and other equipment having separate buttons. Microbes and pathogens can settle and hide between the keys of the keyboard and between buttons of such devices, which can be difficult to clean without disassembling parts of the devices and/or compromising the function of the devices. It is for this reason that flat-like touch screen devices are being used more prevalently in the medical field, since it is easier to clean and sterilize. But, when such touch screen electronic devices used in the medical field are used by a user, it is also important that the user be able to easily confirm that the appropriate function and/or button has been selected. For example, there are situations (for example, when the user needs to visually monitor a patient) in which the user may desire to feel, instead of visualize, that the appropriate function and/or button has been selected. However, as described above, the convention tactile response typically vibrates the whole device or adjacent areas. This can make it difficult, if not impossible, to ensure the appropriate function and/or button was selected as opposed to an adjacent or other function and/or button.

SUMMARY

The present application relates to touch interfaces for electronic devices that localize tactile or haptic feedback responses to specific areas of the touch interface. For example, the tactile response may be localized to a specific location. In this respect, the touch interfaces disclosed herein include recesses and channels on a rear side or underside, opposite the side/surface the user interacts with, in which tactile actuator mechanisms are disposed. The shape and structure of the recesses and channels localize the tactile response to specific areas to prevent the tactile response from propagating to other areas of the touch interface. Thus, when a user selects a specific location on the touchscreen, the tactile response is localized to that location, and the user does not feel the tactile response on other areas of the touch interface.

In an embodiment, the interface includes an outer surface including a selectable area, and a rear surface including a recess corresponding to the selectable area. The recess is adapted to localize a tactile response to the selectable area. A tactile response mechanism may be disposed in the recess and adapted to provide the tactile response.

The recess may include a geometric pattern etched into the recess that is adapted to channel the tactile response and localize the tactile response to a specific area. This prevents the tactile response from propagating to other areas of the interface (for example, a second selectable area adjacent to the selected area). The geometric pattern may be substantially circular, rectangular, or other shape, and includes spokes extending from a substantially central portion of the geometric pattern to a substantially peripheral portion of the geometric pattern.

BRIEF DESCRIPTION OF THE DRAWINGS

Embodiments of devices and methods are illustrated in the figures of the accompanying drawings which are meant to be exemplary and not limiting, in which like references are intended to refer to like or corresponding parts, and in which:

FIG. 4 is a cross-sectional view taken along line 4-4 of the interface of FIG. 2 in accordance with an embodiment of the present application.

FIG. 5 is an enlarged view of a portion of the interface of FIG. 4 in accordance with an embodiment of the present application.

FIG. 6 is an enlarged view of another portion of the interface of FIG. 4 in accordance with an embodiment of the present application.

FIG. 7 is a cross-sectional view taken along line 7-7 of the interface of FIG. 1 in accordance with an embodiment of the present application.

FIG. 8 is an enlarged view of a portion of the interface of FIG. 7 in accordance with an embodiment of the present application.

FIG. 9 is a cross-sectional view taken along line 9-9 of the interface of FIG. 1 in accordance with an embodiment of the present application.

FIG. 10 is an enlarged view of a portion of the interface of FIG. 9 in accordance with an embodiment of the present application.

FIG. 11 is a cross-sectional view taken along line 11-11 of the interface of FIG. 2 in accordance with an embodiment of the present application.

FIG. 12 is an enlarged view of a portion of the interface of FIG. 11 in accordance with an embodiment of the present application.

FIG. 13 is a top plan view of the interface of FIG. 1 including tactile actuators in accordance with an embodiment of the present application.

FIG. 14 is a cross-sectional view taken along line 14-14 of the interface of FIG. 13 in accordance with an embodiment of the present application.

FIG. 15 is an enlarged view of a portion of the interface of FIG. 14 in accordance with an embodiment of the present application.

DETAILED DESCRIPTION

Detailed embodiments of devices and methods are disclosed herein. However, it is to be understood that the disclosed embodiments are merely exemplary of the devices and methods, which may be embodied in various forms. Therefore, specific functional details disclosed herein are not to be interpreted as limiting, but merely as a basis for the claims and as a representative example for teaching one skilled in the art to variously employ the present disclosure.

The present application relates to touch interfaces for electronic devices including one or more tactile feedback response mechanisms. The tactile response mechanisms receive user input and provide a tactile response to the user to indicate that the user has selected a particular location or selectable area on the interface. The underside of the interface includes recesses and channels located in each specific touch or selectable area that localize the tactile response to the individual selectable areas. Thus, when a user selects a specific area, the tactile response is localized to that area, and the user does not feel the tactile response on other areas of the interface.

In an embodiment, the interface may be integrated into and utilized with any number of electronic devices. For example, computers, tablet computers, mobile phones, electronic medical devices (for example, ultrasound machines), and other electronic devices that use touch-screen type interfaces. The interface may also be a single monolithically formed piece without gaps and other areas in which dust, particles, microbes, and/or pathogens can hide. This provides for easy cleaning and disinfecting, which may be beneficial when the interface is integrated into an electronic medical device.

Figure 1:
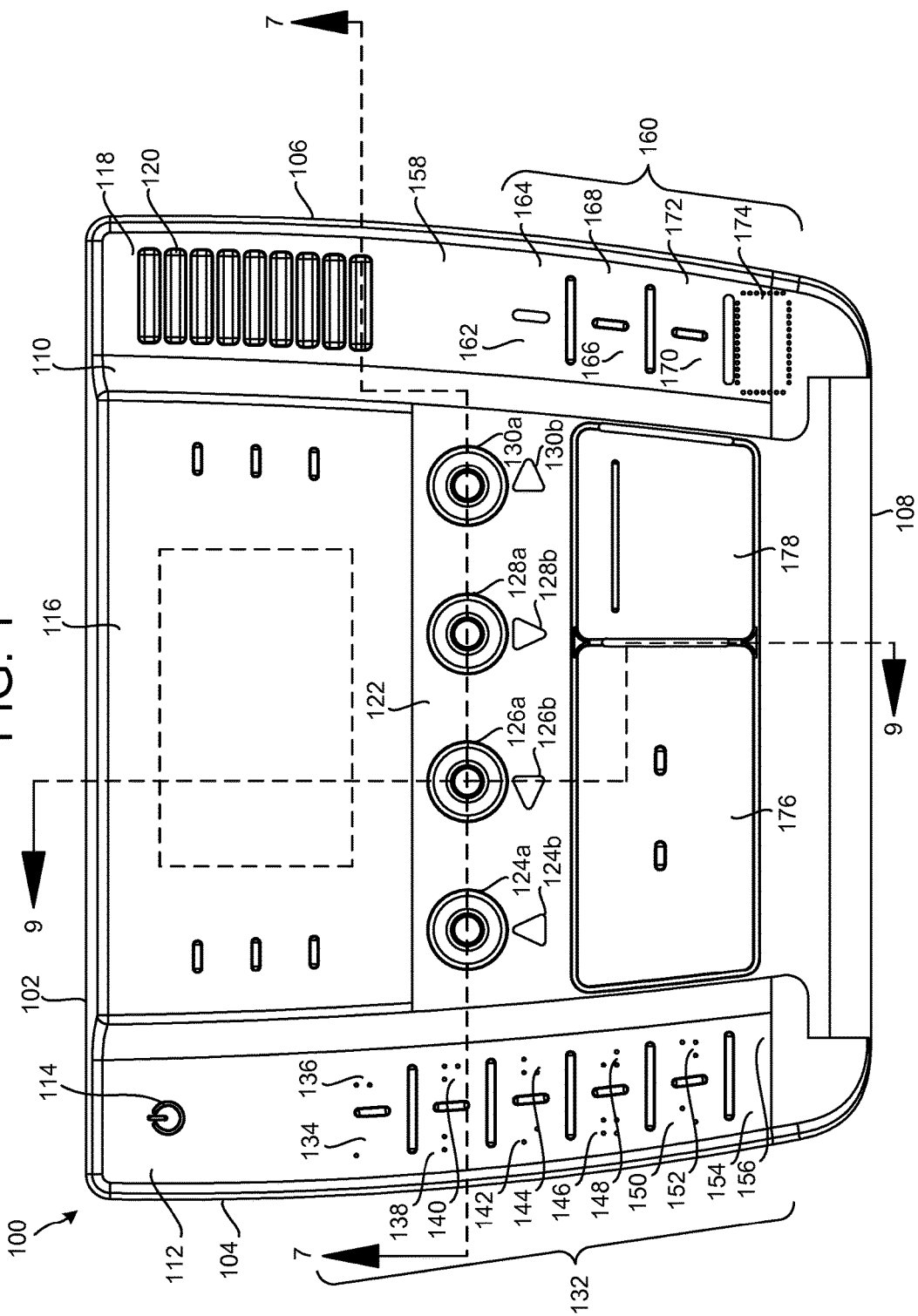
FIG. 1 is a top plan view of an interface for an electronic device in accordance with an embodiment of the present application.
Figure 2:
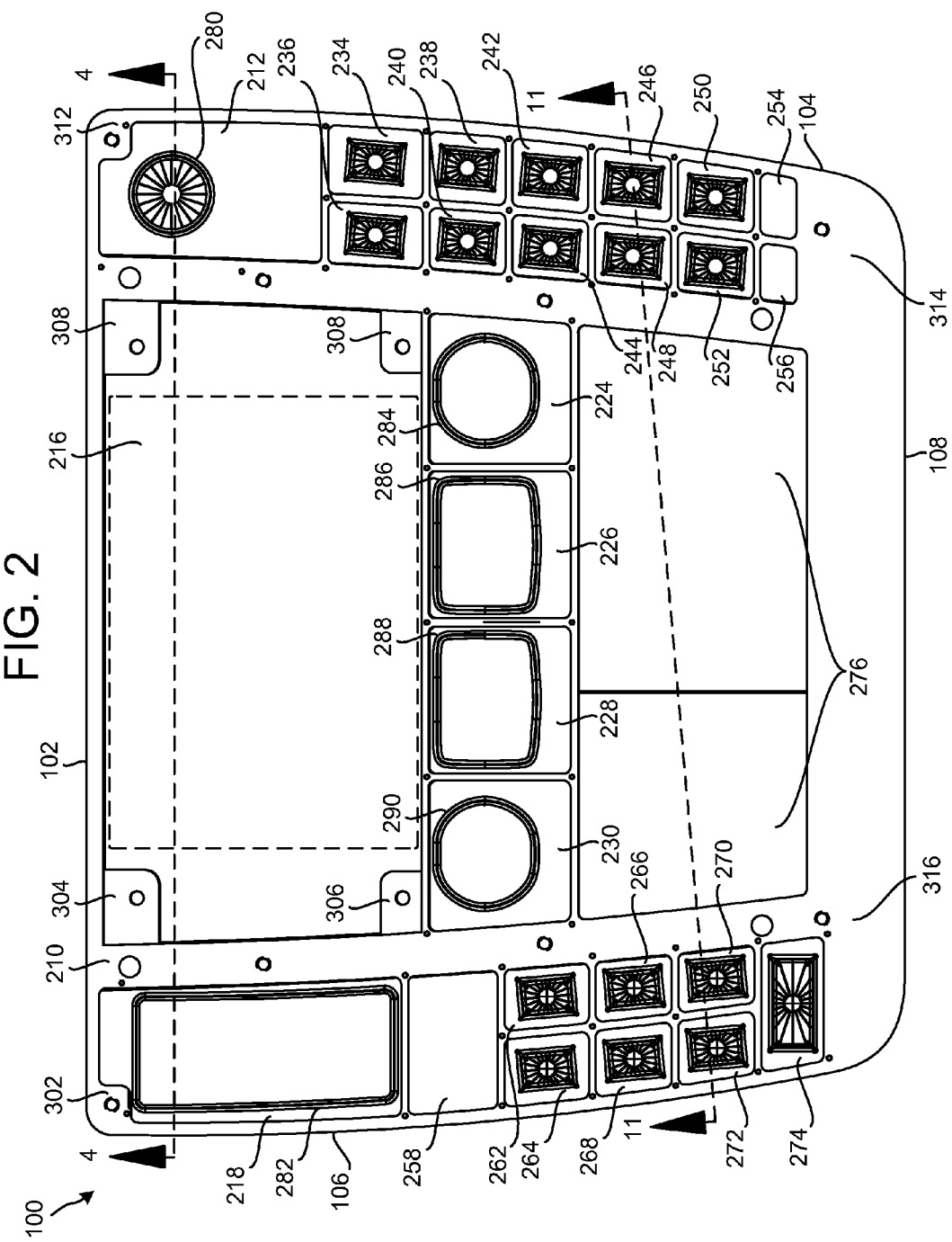
FIG. 2 is a plan view of a rear side of the interface of FIG. 1 in accordance with an embodiment of the present application.
Figure 3:
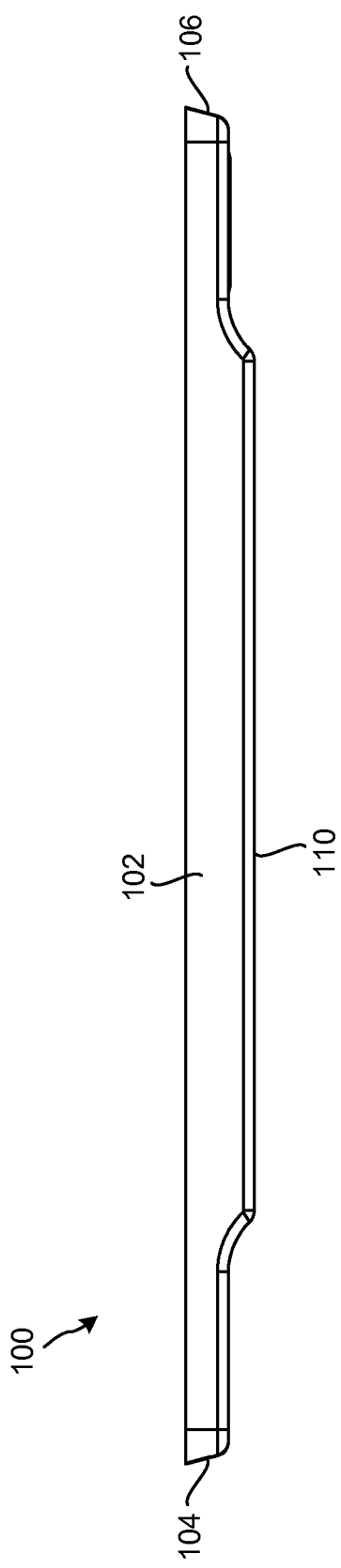
FIG. 3 is a side plan view of the interface of FIG. 1 in accordance with an embodiment of the present application.
Figure 16:
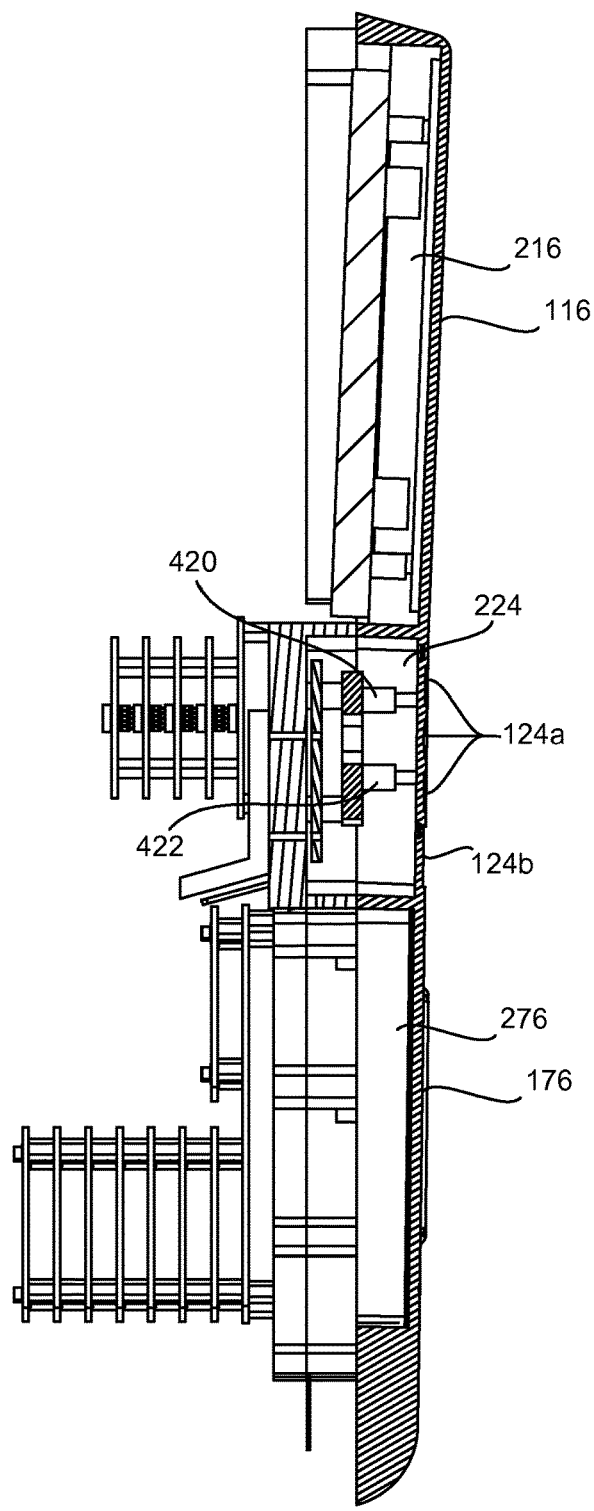
FIG. 16 is a cross-sectional view taken along line 16-16 of the interface of FIG. 13 in accordance with an embodiment of the present application.

FIGS. 1-3 illustrate an embodiment of a touch interface 100 for an electronic device. In one example, the interface 100 may be integrated into and utilized with an ultrasound machine or device. In this respect, the interface 100 may include sides 102-108, an outer surface 110, and a rear surface 210. As described above, the interface 100 may be formed of a single monolithic piece. However, it should be appreciated that the interface 100 may be constructed by coupling numerous components together to form the interface 100.

Referring to FIG. 1, the outer surface 110 of the interface 100 may include a number of areas that a user may interact with, including areas that may be selected by the user, in response a touch of or pressure applied by the user, to perform certain functions and operate the electronic device. For example, the outer surface 110 may include a first area 112 including a selectable power symbol 114 adapted to turn the electronic device on and off; a second area 116 for viewing a display of the electronic device; a third area 118 including one or more selectable slider bar symbols 120; a fourth area 122 including a panel of selectable areas 124a-130b; a fifth area 132 including a panel of selectable areas 134-156; a sixth area 158; a seventh area 160 including a panel of selectable areas 162-174; and eighth and ninth areas 176 and 178.

As illustrated in FIG. 1, the first area 112 may include the selectable power symbol 114 to indicate that touching the selectable power symbol 114 may turn the electronic device on and/or off. The first area 112 may also be used in conjunction with and provide an encoder wheel functionality, as described in further detail below.

The second area 116 may be adapted to be disposed over and/or house a display screen of the electronic device. The second area 116 may also include one or more selectable areas for use in operating the electronic device. The third area 118 may include the one or more slider bar symbols 120 for use in scrolling a display on the display screen up and/or down, provide a zoom function, increase or decrease a level of output of the electronic device, and/or provide another type of functionality or operation of the electronic device.

The fifth area 122 may include the panel of selectable areas 124a-130b. The selectable areas 124a-130b may include indicators that may be adapted to allow the user to select a function or operation to be performed by the electronic device. For example, the selectable areas 124a, 126a, 128a, and 130a may be indicators that are circular in shape that may be indicate that the areas are selectable and/or scrolling wheels. Similarly, the selectable areas 124b, 126b, 128b, and 130b may be up, left, down, and right arrows, respectively.

The fourth area 132 includes the selectable areas 134-156. The selectable areas 134-156 may correspond to a numeric or alpha/numeric panel. The selectable areas 134-156 may also include braille or other tactile indicators to assist the user in selecting a correct areas and/or assist a user that is blind in operating the electronic device. For example, the area 134 may include a braille or other tactile indicator corresponding to the number 1/letter a, the area 136 may include a braille indicator corresponding to the number 2/letter b, the area 138 may include a braille indicator corresponding to the number 3/letter c, the area 140 may include a braille indicator corresponding to the number 4/letter d, the area 142 may include a braille indicator corresponding to the number 5/letter e, the area 144 may include a braille indicator corresponding to the number 6/letter f, the area 146 may include a braille indicator corresponding to the number 7/letter g, the area 148 may include a braille indicator corresponding to the number 8/letter h, the area 150 may include a braille indicator corresponding to the number 9/letter i, and the area 152 may include a braille indicator corresponding to the number 10/letter j. The selectable areas 154 and 156 may also correspond to actions that may be selected or performed for use in selecting and/or operating the functionality of the electronic device.

The sixth area 158 may be adapted to provide one or more selectable areas, and/or be disposed over and/or house a display area of the electronic device; and the seventh area 160 may include the panel of selectable areas 162-174 for use in selecting and/or operating the functionality of the electronic device. The eighth and ninth areas 176 and 178 may also be adapted to provide one or more selectable areas, and/or be disposed over and/or house a display area of the electronic device.

Referring to FIGS. 1 and 2, each of the areas and/or selectable areas described above may correspond to a recess in the rear surface 210 of the interface 100. These recesses serve to separate the areas and/or selectable areas from one another and prevent tactile or haptic responses from propagating between the areas and/or selectable areas, as described in further detail below.

The rear surface 210 may include a number of recesses and/or channels, for example, the rear surface 210 may include a first recess 212 corresponding to the first area 112; a second recess 116 corresponding to the second area 216; a third recess 218 corresponding to the third area 118; recesses 224-230 corresponding to the selectable areas 124a-130b of the fourth area 122, respectively; recesses 234-256 corresponding to the selectable areas 134-156 of the fifth area 132, respectively; a sixth recess 258 corresponding to the sixth area 158; recesses 262-274 corresponding to the selectable areas 162-174 of the seventh area 160, respectively; and an eighth recess 276 corresponding to both of the eighth and ninth areas 176 and 178.

Referring to FIGS. 2, 4, and 5, the first recess 212 corresponding to the first area 112 may include an encoder wheel 280 including spokes etched into or formed in the first recess 212 forming, for example, grooves 502 and 504 (as best illustrated in FIG. 5). The grooves 502 and 504 provide a tactile or haptic geometry that channels the propagation of a tactile or haptic response (for example, vibrations) within the recess 212 to localize the tactile or haptic response within the recess 212. This provides for a tactile or haptic feedback response that the user may feel when the user touches or is touching the first area 112 and/or selectable power symbol 114.

Similar to the first recess 212, referring to FIGS. 2, 4, and 6, the third recess 218 corresponding to the third area 118 is adapted to localize a tactile or haptic response. The third recess 218 may include an area 282 (for example, forming a rectangular shape or other shape) etched into or formed in the first recess 212 forming grooves 602 and 604 (as best illustrated in FIG. 6) that provides a tactile or haptic geometry that channels the propagation of a tactile or haptic response within the recess 218 in order to localize the tactile or haptic response within the recess 218.

Referring to FIGS. 2 and 4, the second recess 116 corresponding to the second area 216 may be adapted to receive a display screen of the electronic device.

Referring to FIGS. 1, 2, and 7-10, the respective recesses 224-230 corresponding to the selectable areas 124a-130b of the fourth area 122 are adapted to localize a tactile or haptic response within the respective recesses. As illustrated in FIG. 2, each of the recesses 224-230 may respectively include geometric patterns 284-290 etched into or formed in the respective recesses 224-230. Referring to FIGS. 7 and 8, for example, the recess 224 may include the geometric pattern 284 (for example, forming a substantially circular shape or other shape) forming grooves 802 and 804. Similarly, referring to FIGS. 9 and 10, the recess 226 may include the geometric pattern 286 (for example, forming a substantially rectangular shape or other shape) forming grooves 1002 and 1004. The geometric pattern 288 and 290 in the recesses 228 and 230, respectively, may be substantially similar to and form grooves similar to the grooves 1002/1004 and 802/804, respectively. The grooves provide a tactile or haptic geometry that channels the propagation of a tactile or haptic response within the respective recesses 224-230 in order to localize the tactile or haptic response within the respective recesses 224-230 and to the corresponding selectable areas 124a-130b. Moreover, the grooves effectively disassociates the respective recess with adjacent recesses.

Referring to FIGS. 1, 2, 11, and 12, the respective recesses 234-256 corresponding to the selectable areas 134-156 of the fifth area 132 and the respective recesses 262-274 corresponding to the selectable areas 162-174 of the seventh area 160 are also adapted to localize a tactile or haptic response within the respective recesses. For example, the recess 270 includes a geometric pattern 292 (for example, forming a substantially rectangular shape having a central portion and spokes extending from the central portion, or other shape) etched into or formed in the recess 270. Referring to FIGS. 11 and 12, the geometric pattern 292 forms grooves 1202 and 1204. The grooves 1202 and 1204 provide a tactile or haptic geometry that channels the propagation of a tactile or haptic response within the recess 270 in order to localize the tactile or haptic response within the respective recess 270 and disassociates the respective recess 270 from adjacent recesses. The other recesses, including recesses 234-252, 262-268 and 272 and 274, also include geometric patterns forming grooves substantially similar to the recess 270.

As illustrated in FIG. 2, the recesses 254 and 256 do not include any grooves; however, the recesses 254 and 256 may include grooves providing a tactile or haptic geometry similar to that described above. The sixth recess 258 corresponding to the sixth area 158 and the eighth recess 276 corresponding to both of the eighth and ninth areas 176 and 178 also do not include any grooves; however, the recesses 258 and 276 may also include grooves providing a tactile or haptic geometry similar to that described above.

The interface 100 may also include one or more connector portions 302-316 including fastener apertures adapted to receive fasteners to couple the interface 100 to the electronic device. The fasteners may be screws, nails, pins, rivets, adhesives, or other fastening mechanisms.

As described above, the recesses and grooves are adapted to contain the propagation of a tactile or haptic response, for example, from a tactile/haptic actuator, within the respective recesses and to the corresponding selectable areas. FIG. 13 is similar to FIG. 1 in that it illustrates a plan view of the interface 100; however, as is illustrated in the cross-sectional views of FIGS. 14-16, FIG. 13 includes one or more tactile/haptic actuators disposed within the recesses. For the sake of brevity, the tactile/haptic actuators are described with reference to a few recesses with the understanding that the other recesses may also include substantially similar components.

Referring to FIGS. 13-15, the recess 250 corresponding to the selectable area 150 may include grooves 1502 and 1504 forming a tactile/haptic geometry. An actuator mechanism 402 may be disposed in and be adapted to provide a tactile/haptic response to a user touching the selectable area 150. Referring to FIG. 15, the actuator mechanism 402 may be a piezoelectric actuator and include an actuator portion 404 and a piezoelectric portion 406 to provide the tactile/haptic response. A sensor 408 may also be disposed in the area including the grooves 1502 and 1504, and an end of the actuator portion 404 may be disposed proximate the sensor 408. When a user touches the selectable area 150, the sensor 408 may detect that a touch has occurred and cause the actuator mechanism 402 to provide a tactile/haptic response (for example, in the form of a vibration) to the recess 250 including the grooves 1502 and 1504 to indicate to the user that the selectable area 150 has been selected.

As described above, the recess, for example, recess 250, and the area including the grooves in the recess, for example, the grooves 1502 and 1504, channel the tactile/haptic response and contain the tactile/haptic response to the selectable area, for example, the selectable area 150. Thus, the tactile/haptic response should only be felt by the user in the area of the selectable area 150, and not in any other area of the interface 100.

The actuator mechanism 402 may be held in place by one or more housing portions of the electronic device, such as, housing portions 410/412. It should be appreciated that the actuator mechanism 402 and the sensor 408 may be electrically coupled to a processor adapted to control and implement the touch functionality and instruct the actuator mechanism 402 to provide the tactile/haptic response in response to the sensor 408 detecting a touch of the user.

The other recesses described above, may also include substantially similar components, for example, one or more actuator mechanisms. For example, as illustrated in FIG. 14, the recess 252 corresponding to the selectable area 152 may include an actuator mechanism 414, the recess 270 corresponding to the selectable area 170 may include an actuator mechanism 416, and the recess 272 corresponding to the selectable area 172 may include an actuator mechanism 418. Similarly, referring to FIG. 16, the recess 224 corresponding to the selectable areas 124a-b may include actuator mechanisms 420 and 422.

Although the devices and methods have been described and illustrated in connection with certain embodiments, many variations and modifications will be evident to those skilled in the art and may be made without departing from the spirit and scope of the present disclosure.

For example, it should be appreciated that the interface 100 described above corresponds to and includes selectable areas, recesses and tactile/haptic geometry for an ultrasound machine. Any number of recesses in any location may be formed in an interface to correspond to selectable areas of any electronic device, and a tactile/haptic geometry may be formed in any of the recesses in accordance with the present disclosure.

The present disclosure is thus not to be limited to the precise details of methodology or construction set forth above as such variations and modification are intended to be included within the scope of the present disclosure. Moreover, unless specifically stated any use of the terms first, second, etc. do not denote any order or importance, but rather the terms first, second, etc. are merely used to distinguish one element from another.

What is claimed is:

1. A touch interface comprising:
   a front surface including a selectable area;
   a rear surface including a recess corresponding to the selectable area and grooves formed by a geometric pattern etched into the recess; and
   a tactile response mechanism disposed in the recess and adapted to provide a tactile response to a user in response to the user selecting the selectable area, wherein the grooves channel propagation of and localize the tactile response to the selectable area and limit propagation of the tactile response to outside of the selectable area, wherein the geometric pattern is substantially circular or rectangular and includes spokes each extending from a substantially central portion of the geometric pattern to a substantially peripheral portion of the geometric pattern.

2. The interface of claim 1, wherein the front surface includes a symbol located on the selectable area to identify a function when selection of the selectable area occurs.

3. The interface of claim 1, wherein the tactile response mechanism is a piezoelectric actuator.

4. The interface of claim 1, further comprising a sensor disposed in the recess and adapted to detect a touch applied by the user and cause the tactile response mechanism to provide the tactile response.

5. A selectable interface comprising:
   a front surface including a selectable area; and
   a rear surface including a recess corresponding to the selectable area and grooves formed by a geometric pattern etched into the recess, wherein the grooves channel propagation of and to localize a tactile response to the selectable area and limit propagation of the tactile response to other areas outside of the selectable area, wherein the geometric pattern is substantially circular or rectangular and includes spokes each extending from a substantially central portion of the geometric pattern to a substantially peripheral portion of the geometric pattern.

6. The interface of claim 5, wherein the front surface includes a symbol located on the selectable area to identify a function when selection of the selectable area occurs.

7. A selectable interface comprising:
   an outer surface including first and second selectable areas; and
   a rear surface including:
      a first recess corresponding to the first selectable area and first grooves formed by a first geometric pattern etched into the first recess, wherein the first grooves channel propagation of and adapted to localize a first tactile response to the first selectable area and prevent the first tactile response from propagating to the second selectable area, and
      a second recess corresponding to the second selectable area, wherein the second recess is adapted to localize a second tactile response to the second selectable area and prevent the second tactile response from propagating to the first selectable area, wherein the first geometric pattern includes spokes each extending from a substantially central portion of the first geometric pattern to a substantially peripheral portion of the first geometric pattern.

8. The interface of claim 7, wherein the first and second selectable areas are adjacent to each other.

9. The interface of claim 7, further comprising:
   a first piezoelectric actuator disposed in the first recess and adapted to provide the first tactile response to a user in response to the user selecting the first selectable area; and
   a second piezoelectric actuator disposed in the second recess and adapted to provide the second tactile response to the user in response to the user selecting the second selectable area.

10. The selectable interface of claim 7, wherein the outer surface and the rear surface are formed from a single monolithic piece.

11. The selectable interface of claim 9, further comprising:
   a processor electrically coupled to the first and second piezoelectric actuators and configured to control and implement the first tactile response and the second tactile response through actuation of the first and second piezoelectric actuators.

12. The selectable interface of claim 7, wherein the first recess corresponding to the first selectable area comprises an encoder wheel.

* * * * *